(12) United States Patent
Hong et al.

(10) Patent No.: US 10,590,050 B2
(45) Date of Patent: Mar. 17, 2020

(54) METHOD FOR CO-PRODUCING VARIOUS ALKENYL HALIDES AND HYDROFLUOROALKANES

(71) Applicant: Zhejiang Quhua Fluor-Chemistry Co Ltd, Zhejiang (CN)

(72) Inventors: Jiangyong Hong, Zhejiang (CN); Bo Yang, Zhejiang (CN); Yan Zhang, Zhejiang (CN); Guojun Yu, Zhejiang (CN); Yang Zhao, Zhejiang (CN); Hao Ouyang, Zhejiang (CN); Haitao Gong, Zhejiang (CN)

(73) Assignee: Zhejiang Quhua Fluor-Chemistry Co Ltd, Zhejiang (CN)

(*) Notice: Subject to any disclaimer, the term of this patent is extended or adjusted under 35 U.S.C. 154(b) by 0 days.

(21) Appl. No.: 16/337,407

(22) PCT Filed: Jun. 25, 2018

(86) PCT No.: PCT/CN2018/000232
§ 371 (c)(1),
(2) Date: Mar. 28, 2019

(87) PCT Pub. No.: WO2019/047447
PCT Pub. Date: Mar. 14, 2019

(65) Prior Publication Data
US 2020/0031742 A1 Jan. 30, 2020

(30) Foreign Application Priority Data
Sep. 7, 2017 (CN) .......................... 2017 1 0798254

(51) Int. Cl.
*C07C 17/20* (2006.01)
*B01J 21/04* (2006.01)
(Continued)

(52) U.S. Cl.
CPC ............. *C07C 17/206* (2013.01); *B01J 21/04* (2013.01); *B01J 23/26* (2013.01); *B01J 23/58* (2013.01);
(Continued)

(58) Field of Classification Search
CPC ..... C07C 17/206; C07C 17/21; C07C 17/358; C07C 17/383; C07C 17/38; C07C 21/18;
(Continued)

(56) References Cited

U.S. PATENT DOCUMENTS

| | | | |
|---|---|---|---|
| 2012/0123172 A1* | 5/2012 | Hibino | B01J 21/04 570/160 |
| 2015/0099907 A1* | 4/2015 | Imura | C07C 17/358 570/151 |

FOREIGN PATENT DOCUMENTS

| | | |
|---|---|---|
| CN | 101028992 | 9/2007 |
| CN | 102918010 | 2/2013 |

(Continued)

OTHER PUBLICATIONS

"International Search Report (Form PCT/ISA/210)", dated Sep. 20, 2018, with English translation thereof, pp. 1-4.

*Primary Examiner* — Jafar F Parsa
(74) *Attorney, Agent, or Firm* — JCIPRNET

(57) ABSTRACT

Disclosed is a method for co-producing various alkenyl halides and hydrofluoroalkanes: cis-1-chloro-3,3,3-trifluoropropene is introduced into a first reactor to carry out an isomerization reaction in the presence of a first catalyst, and the reaction product is rectified to obtain a product trans-1-chloro-3,3,3-trifluoropropene; and 30-70 wt % of trans-1-chloro-3,3,3-trifluoropropene and hydrogen fluoride are mixed and then introduced into a second reactor to carry out a reaction in the presence of a second catalyst to obtain a second reactor reaction product; the second reactor reaction product is introduced into a phase separator for separation, (Continued)

and the obtained organic phase is rectified to obtain the products trans-1,3,3,3-tetrafluoropropene, cis-1,3,3,3-tetrafluoropropene and 1,1,1,3,3-pentafluoropropane. The invention has the advantages of simple process, high efficiency, high operation flexibility, less investment and low energy consumption.

8 Claims, 1 Drawing Sheet

(51) Int. Cl.
  *B01J 23/26*  (2006.01)
  *C07C 17/21*  (2006.01)
  *C07C 17/358*  (2006.01)
  *B01J 23/60*  (2006.01)
  *B01J 23/62*  (2006.01)
  *C07C 17/383*  (2006.01)
  *C07C 21/18*  (2006.01)
  *B01J 23/58*  (2006.01)

(52) U.S. Cl.
  CPC ............... *B01J 23/60* (2013.01); *B01J 23/62* (2013.01); *C07C 17/21* (2013.01); *C07C 17/358* (2013.01); *C07C 17/383* (2013.01); *C07C 21/18* (2013.01)

(58) Field of Classification Search
  CPC ... B01J 23/26; B01J 21/04; B01J 23/62; B01J 23/58; B01J 23/60
  See application file for complete search history.

(56) References Cited

FOREIGN PATENT DOCUMENTS

| | | |
|---|---|---|
| CN | 103189338 | 7/2013 |
| CN | 103209942 | 7/2013 |
| CN | 103429558 | 12/2013 |
| CN | 103476736 | 12/2013 |
| CN | 103880589 | 6/2014 |
| CN | 107522592 | 12/2017 |
| WO | 2016194794 | 12/2016 |

* cited by examiner

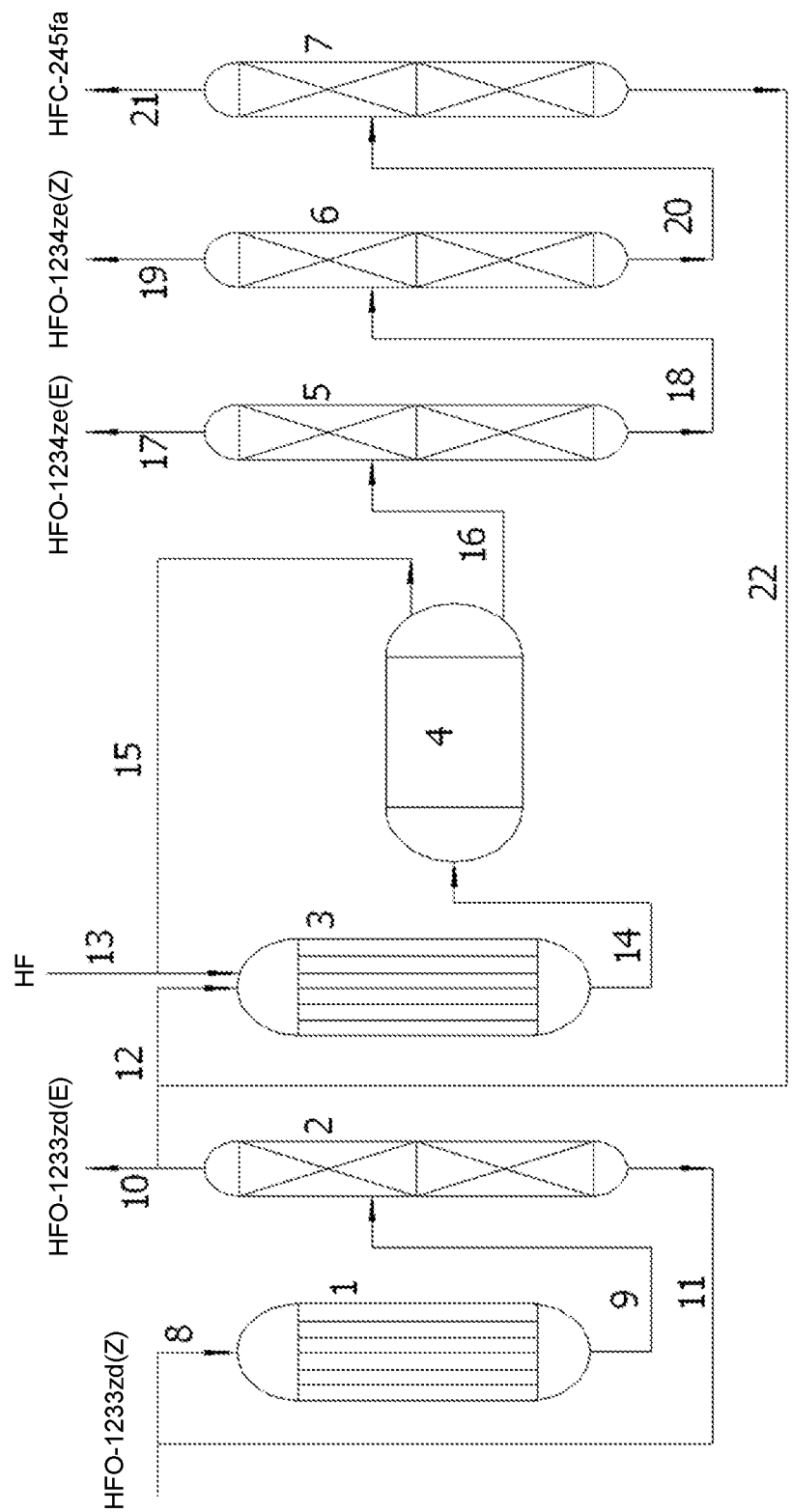

METHOD FOR CO-PRODUCING VARIOUS ALKENYL HALIDES AND HYDROFLUOROALKANES

CROSS-REFERENCE TO RELATED APPLICATION

This application is a 371 of international application of PCT application serial no. PCT/CN2018/000232, filed on Jun. 25, 2018, which claims the priority benefit of China application no. 201710798254.6, filed on Sep. 7, 2017. The entirety of each of the above-mentioned patent applications is hereby incorporated by reference herein and made a part of this specification.

BACKGROUND OF THE INVENTION

1. Technical Field

The invention relates to preparation methods of alkenyl halides, chlorofluoroolefins, and hydrofluoroalkanes, in particular to a method for co-producing various alkenyl halides and hydrofluoroalkanes.

2. Background Art 1,3,3,3-tetrafluoropropene (HFO-1234ze), belonging to the HFO series, is an important fourth-generation refrigerant and foaming agent. There are two types of HFO-1234ze: Z-type (HFO-1234ze(Z)) and E-type (HFO-1234ze(E)); the Z-type (HFO-1234ze(Z)) has a boiling point of 9° C., and the E-type (HFO-1234ze(E)) has a boiling point of −19° C. and a GWP of 6. The Z-type (HFO-1234ze(Z)) can be used as a foaming agent, and the E-type (HFO-1234ze(E)) can be compounded with other materials to serve as refrigerants.

There are two types of 1-chloro,3,3,3-trifluoropropene (HFO-1233zd): Z-type (HFO-1233zd(Z)) and E-type (HFO-1233zd(E)); the E-type (HFO-1233zd(E)) has a boiling point of 19° C., and the Z-type (HFO-1233zd(Z)) has a boiling point of 38° C., a life cycle climate performance (LCCP) value of 26 days, an ozone depletion potential (ODP) value of about 0 and a global warming potential (GWP) value of less than 5. The E-type (HFO-1233zd(E)) is the first choice for a new generation of environmentally friendly foaming agent and is suitable for the foaming of polyurethane thermal insulation materials in the fields of household appliances, thermal insulation in building, cold chain transportation and thermal insulation in industry. The E-type (HFO-1233zd(E)) is the best alternative foaming agent for CFCs, HCFCs, HFCs and other non-fluorocarbon foaming agents. Compared with the existing foaming agent systems (HFC-245fa and cyclopentane), it has better thermal conductivity and overall energy consumption. Compared with the same model of HFC-245fa and cyclopentane refrigerators, an HFO-1233zd(E) refrigerator is reduced in thermal conductivity by 7% (compared with the HFC-245fa system) and 12% (compared with the cyclopentane system), respectively, and is reduced in overall energy consumption by 3% (compared with the HFC-245fa system) and 7% (compared with the HFC-245fa system), respectively.

1,1,1,3,3-pentafluoropropane (HFC-245fa) which is a safe fluorinated hydrocarbon for the ozone layer, has value of ozone depletion potential (ODP) of 0 and low value of global warming potential (GWP), is non-inflammable and low-toxicity. The HFC-245fa is currently used as a substitute for chlorotrifluoromethane (CFC-11) and 1,1,1-trichlorofluoroethane (HCFC-141b) foaming agents and also widely used in solvents, propellants, fire extinguishing agents and dry etchants.

The preparation method of HFO-1233zd is implemented by a gas phase synthesis method with 1,1,1,3,3-pentachloropropane (HCC-240fa) and HF as main raw materials. After the reaction, two types, Z-type (HFO-1233zd(Z)) and E-type (HFO-1233zd(E)) are produced. At present, the Z-type (HFO-1233zd(Z)) is less used, so Z-type (HFO-1233zd(Z)) is also isomerized into E-type (HFO-1233zd(E)).

The preparation method of HFC-245fa is mainly implemented by a liquid phase method with 1,1,1,3,3-pentachloropropane and anhydrous hydrogen fluoride as main raw materials, where a chloride of Sb, Sn or Ti is generally used as a catalyst, the reaction temperature and energy consumption are low, but equipment is seriously corroded, the operation is in an intermittent manner, and environmental protection issues are outstanding.

There are mainly two synthetic routes of HFO-1234ze that have industrial prospects: a gas phase dehydrofluorination method of 1,1,1,3,3-pentafluoropropane (HFC-245fa) and an HF addition method of 1-chloro, 3,3,3-trifluoropropene.

Chinese Patent Publication No. CN103189338A for an invention entitled "Integrated Process to Coproduce Trans-1-chloro-3,3,3-trifluoropropene, Trans-1,3,3,3-tetrafluoropropene and 1,1,1,3,3-pentafluoropropane", published on Jul. 3, 2013. The invention discloses an integrated production process for coproducing trans-1-chloro-3,3,3-trifluoropropene, trans-1,3,3,3-tetrafluoropropene and 1,1,1,3,3-pentafluoropropane starting from a single chlorohydrocarbon raw material 1,1,1,3,3-pentachloropropane. The process comprises a liquid or gas phase reaction/purification operation that directly produces a conjugation of trans-1-chloro-3,3,3-trifluoropropene. In a second liquid phase fluorination reactor, trans-1-chloro-3,3,3-trifluoropropene comes in contact with hydrogen fluoride (HF) in the presence of a catalyst to produce 1,1,1,3,3-pentafluoropropane through a reaction with a high conversion rate and high selectivity. A third reactor is used to produce trans-1,3,3,3-tetrafluoropropene by contact with a caustic solution in a liquid phase or by dehydrofluorination of 245fa using a dehydrofluorination catalyst in a gas phase. One or more purification processes may be performed after this operation to recycle the trans-1,3,3,3-tetrafluoropropene product. The shortcomings of liquid phase fluorination and liquid phase dehydrofluorination are that the reaction catalyst has a short life, and the whole process produces lots of waste liquid, and the environmental protection treatment cost is high.

Chinese Patent Publication No. CN103476736A for an invention entitled "Integrated Process to Co-produce 1,1,1,3,3-pentafluoropropane, Tran-1-chloro-3,3,3-trifluoropropene, and Trans-1,3,3,3-tetrafluoropropene", published Dec. 25, 2013. The invention discloses a fully integrated process for preparing 1,1,1,3,3-pentafluoropropane (HFC-245fa), trans-1-chloro-3,3,3-trifluoropropene (HFO-1233zd(E)) and trans-1,3,3,3-tetrafluoropropene (HFO-1234ze(E)). The chemical process comprises: (a) reacting 1,1,1,3,3-pentachloropropane (HCC-240fa) or its derivative selected from 1,1,3,3-tetrachloropropene and 1,3,3,3-tetrachloropropene with excessive anhydrous HF in a certain manner in a liquid phase reactor in the presence of a catalyst to co-produce HFO-1233zd, HFO-1234ze, HCFC-244fa (3-chloro-1,1,1,3-tetrafluoropropane) and HFC-245fa in a first reactor; (b) reacting HFO-1233zd and HFO-1234ze with excessive HCl in a second reactor in the presence of a catalyst to separately convert the two olefins to HCFC-243fa and HCFC-244fa;

(c) reacting HCFC-243fa and HCFC-244fa in a third reactor in the presence of a dehydrochlorination catalyst or in a caustic solution to form HFO-1233zd and HFO-1234ze; and (d) reacting HFO-1233zd(Z) and HFO-1234ze(Z) in a fourth reactor in the presence of a catalyst to form HFO-1233zd(E) and HFO-1234ze(E), respectively. Liquid phase reactions take place in the first and second steps of the route, the reaction catalysts have a short life, and the whole process produces lots of waste liquid, and the environmental protection treatment cost is high.

Chinese Patent Publication No. CN103429558A for an invention entitled "Integrated Process to Co-produce Trans-1-chloro-3,3,3-trifluoropropene, Trans-1,3,3,3-tetrafluoropropene and 1,1,1,3,3-pentafluoropropane", published Dec. 4, 2013. This cooperation is generally a three-step process. The chemical process involves the steps of: (1) reacting HCC-240fa with excessive HF in a liquid phase catalytic reactor in such a manner as to primarily produce HFO-1233zd(E), HCFC-244fa and HCl; (2) then directly producing any of the three desired products by using a HCFC-244fa material flow; (3a) dehydrochlorinating the HCFC-244fa material flow to produce the desired second product HFO-1234ze(E); and/or (3b) if more HFO-1233zd(E) is required, dehydrofluorinating HCFC-244fa to produce HFO-1233zd (E); and/or (3c) further fluorinating HCFC-244fa to form HFC-245fa.

Chinese Patent Publication No. CN102918010A for an invention entitled "Integrated Process to Co-produce Trans-1-chloro-3,3,3-trifluoropropene and Trans-1,3,3,3-tetrafluoropropene", published Feb. 25, 2015. Disclosed is an integrated manufacturing process comprising a combination of liquid phase reaction and purification operation for the direct production of trans-1-chloro-3,3,3-trifluoropropene and 3-chloro-1,1,1,3-tetrafluoropropene which is a precursor for the manufacture of trans-1,3,3,3-tetrafluoropropene. The mixture of the co-products is easily separated by conventional distillation, and then 3-chloro-1,1,1,3-tetrafluoropropane is dehydrochlorinated by contact with a caustic solution in a liquid phase or by using a dehydrochlorination catalyst in a gas phase to produce trans-1,3,3,3-tetrafluoropropene. The shortcomings of liquid phase fluorination and liquid phase dehydrofluorination are that the reaction catalyst has a short life, and the whole process produces lots of waste liquid, and the environmental protection treatment cost is high.

Chinese Patent Publication No. CN103880589A for an invention entitled "Process for Co-producing HFO-1234ze and HFC-245fa, published Jun. 25, 2014. HFO-1234ze and HFC-245fa are prepared by two-stage gas phase fluorination using 1,1,1,3,3-pentachloropropane (HCC-240fa) and HF as raw materials. HCC-240fa reacts with HF in a first reactor to obtain HFC-245fa, HFO-1233zd, HF, HCl. After HCl is separated, the mixture flow enters a second reactor to obtain HFO-1234ze(Z), HFO-1234ze(E), HFO-1233zd, HFC-245fa and HCFC-244fa. The mixture flow is subjected to a series of separations to obtain HFC-245fa and HFO-1234ze.

SUMMARY OF THE INVENTION

The invention is directed to the shortcomings of the prior art, and provides a method for co-producing various alkenyl halides and hydrofluoroalkanes with simple process, high operation flexibility, low investment and low energy consumption.

In order to solve the above technical problems, the technical solution adopted by the invention is: a method for co-producing various alkenyl halides and hydrofluoroalkanes, comprising the following steps:

(a) introducing cis-1-chloro-3,3,3-trifluoropropene into a first reactor where an isomerization reaction occurs in the presence of a first catalyst to obtain a first reactor reaction product, wherein the reaction temperature is 200-400° C., and the air velocity is 300-1000 $h^{-1}$;

(b) introducing the first reactor reaction product obtained in Step (a) into a first rectification column to obtain a product trans-1-chloro-3,3,3-trifluoropropene and a first rectification column bottom liquid;

(c) mixing 30-70 wt % (mass percentage) of trans-1-chloro-3,3,3-trifluoropropene obtained in Step (b) with hydrogen fluoride, and then introducing in a second reactor where a reaction occurs in the presence of a catalyst to obtain a second reactor reaction product, wherein the molar ratio of hydrogen fluoride to trans-1-chloro-3,3,3-trifluoropropene is 8-20:1, the reaction temperature is 180-400° C., and the space velocity is 300-1000 $h^{-1}$;

(d) introducing the second reactor reaction product obtained in Step (c) into a phase separator for separation to obtain an inorganic phase and an organic phase;

(e) introducing the organic phase obtained in Step (d) into a second rectification column to obtain a trans-1,3,3,3-tetrafluoropropene product and a second rectification column bottom liquid;

(f) introducing the second rectification column bottom liquid obtained in Step (e) into a third rectification column to obtain a cis-1,3,3,3-tetrafluoropropene product and a third rectification column bottom liquid; and (g) introducing the third rectification column bottom liquid obtained in Step (f) into a fourth rectification column to obtain a 1,1,1,3,3-pentafluoropropane product and a fourth rectification column bottom liquid.

As a preferred embodiment of the invention, the first rectification column bottom liquid in Step (b) can be recycled back to the first reactor.

As a preferred embodiment of the invention, the inorganic phase in Step (d) can be recycled back to the second reactor.

As a preferred embodiment of the invention, the fourth rectification column bottom liquid in Step (g) can be recycled back to the second reactor.

As a preferred embodiment of the invention, the reaction temperature in Step (a) is preferably 250-320° C., and the space velocity is preferably 500-800 $h^{-1}$.

As a preferred embodiment of the invention, the molar ratio of hydrogen fluoride to trans-1-chloro-3,3,3-trifluoropropene in Step (c) is preferably 10-15:1, the reaction temperature is preferably 200-350° C., and the space velocity is preferably 500-700 $h^{-1}$.

As a preferred embodiment of the invention, the first catalyst in Step (a) is alumina-loaded chromium and magnesium, wherein the load of chromium is preferably 3-8 wt %, and the load of magnesium is preferably 1-3 wt %.

As a preferred embodiment of the invention, the second catalyst in Step (c) preferably comprises, by mass percentage, 73-90% of chrome oxide, 9.5-25% of zinc oxide, and 0.5-2% of gallium oxide.

In the invention, the isomerization reaction occurs in the first reactor to isomerize HFO-1233zd(Z) to HFO-1233zd(E). Since the isomerization is an equilibrium reaction, the conversion rate of HFO-1233zd(Z) is significantly influenced by temperature; when the temperature is high, a chlorinated olefin easily carbonizes the catalyst. Therefore, the reaction conditions in the first reactor of the invention are controlled such that the reaction temperature is 200-400° C. and the space velocity is 300-1000 $h^{-1}$; and the reaction conditions are preferably that: the reaction temperature is 250-320° C., and the space velocity is 500-800 h$^{-1}$.

In the invention, HFO-1233zd(E) and hydrogen fluoride (HF) are reacted in a second reactor to obtain a mixture containing HFC-245fa, HFO-1234ze(E) and HFO-1234ze (Z), and the reaction is as follows:

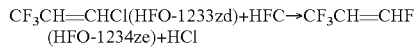
CF$_3$CH═CHCl(HFO-1233zd)+HFC→CF$_3$CH═CHF (HFO-1234ze)+HCl

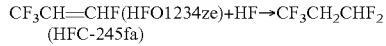
CF$_3$CH═CHF(HFO1234ze)+HF→CF$_3$CH$_2$CHF$_2$ (HFC-245fa)

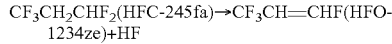
CF$_3$CH$_2$CHF$_2$(HFC-245fa)→CF$_3$CH═CHF(HFO-1234ze)+HF

Alternatively, CF$_3$CH═CHCl and HF are reacted to obtain CF$_3$CH$_2$CHFCl, then dehydrochlorination (HCl) is carried out to obtain CF$_3$CH═CHF, and CF$_3$CH$_2$CHF$_2$ also can be obtained through a one-step reaction between CF$_3$CH═CHCl and HF.

Multiple reactions in the second reactor are carried out simultaneously, which are greatly affected by the reaction conditions. When the temperature rises, the content of HFC-245fa decreases and the content of HFO-1234ze increases. Low temperature is favorable for the formation of HFC-245fa. At a temperature of 210-230° C., the content of HFC-245fa produced is the highest. The temperature rise is favorable for the formation of HFO-1234ze. At a temperature of 330-350° C., the content of HFO-1234ze produced is highest. HFO-1234ze is a mixture of HFO-1234ze(Z) and HFO-1234ze(E), and the proportion of products can be adjusted according to market demands. The temperature is high, the olefin raw material CF3CH═CHCl is easy to self-polymerize, the catalyst is carbonized and deactivated faster. The catalyst is mainly composed of chromium oxide, and also comprises oxides of zinc and gallium. The addition of zinc increases the activity of the catalyst, and the addition of gallium improves the selectivity of the target product, prevents the formation of other by-products and also inhibits the carbonation of the catalyst under a high temperature condition. The molar ratio has a certain influence on the selectivity of the product. If the molar ratio is increased, the content of HFC-245fa is increased, and the content of HFO-1234ze is decreased. If the molar ratio is high, excessive HF can carry away heat, which is advantageous for prolonging the life of the catalyst. Therefore, the reaction conditions in the second reactor of the invention are controlled such that the molar ratio of HF to HFO-1233zd(E) is 8-20:1, the reaction temperature is 180-400° C., and the space velocity is 300-1000 h$^{-1}$. The conditions are preferably such that the molar ratio of HF to HFO-1233zd(E) is 10-15:1, the reaction temperature is 200-350° C., and the space velocity is 500-700 h$^{-1}$.

The second reactor reaction product contains an unreacted raw material HFO-1233zd(E) and excessive HF in addition to the products HFC-245fa, HFO-1234ze(E) and HFO-1234ze(Z). The boiling points of these substances are as follows:

| Substance | Boiling point (° C.) |
|---|---|
| HF | 19.5 |
| HFC-245fa | 15.3 |
| HFO-1234ze(E) | −19 |
| HFO-1234ze(Z) | 9 |
| HFO-1233zd(E) | 19 |

Since the boiling points of HF, HFC-245fa and HFO-1233zd(E) are very close, HF is left two much and needs to be recycled, which makes the subsequent separation difficult. The invention designs a phase separator in the separation step so that the inorganic phase HF and the organic phase are effectively separated, and the temperature of the phase separator is controlled to be 0 to −30° C. 99% of the HF is separated and returned to the second reactor for recycling.

The first reactor catalyst of the invention is alumina-loaded chromium and magnesium, and can be prepared by a dipping method known in the art: chlorides or nitrates of the metals chromium and magnesium are dissolved in water to soak an alumina carrier; after a certain loading level is reached, drying, calcination, and fluorination with HF are carried out to obtain the catalyst.

The second reactor catalyst of the invention mainly comprises chromium oxide, and further comprises oxides of zinc and gallium, and can be prepared by a coprecipitation method known in the art: chlorides or nitrates of chromium, zinc and gallium are dissolved in water in a certain ratio and added with a precipitant to react, wherein the precipitant may be a weak base such as NH$_3$.H$_2$O or (NH$_4$)$_2$.CO$_3$, then the reaction product is filtered, washed with water, dried, calcined, granulated, and tableted into a precursor, and then the precursor is fluorinated to obtain the catalyst.

The first reactor and the second reactor in the invention may be of an isothermal or adiabatic type.

Compared with the prior art, the invention has the following advantages:

1. The process is simple and the efficiency is high. The invention adopts a two-step gas phase reaction, and by optimizing the reaction process, the catalyst ratio, the reaction temperature, the space velocity and other parameters, the reaction efficiency is improved and the energy consumption is remarkably reduced.

2. The invention is environmentally friendly and generates less three wastes. The invention adopts a gas phase production process, and the unreacted raw materials and intermediate products can be recycled into the reactors to continue the reaction, which significantly reduces the discharge of the three wastes;

3. The investment is small and the operation flexibility is high. A set of equipment can simultaneously four produces: trans-1-chloro-3,3,3-trifluoropropene, trans-1,3,3,3-tetrafluoropropene, cis-1,3,3,3-tetrafluoropropene and 1,1,1,3,3-pentafluoropropane; the proportion of products can be flexibly adjusted according to market demands, thus significantly reducing equipment investment.

BRIEF DESCRIPTION OF THE DRAWING

FIG. 1 is a process flow diagram of the invention.

As shown in the FIGURE: 1 refers to first reactor, 2 refers to first rectification column, 3 refers to second reactor, 4 refers to phase separator, 5 refers to second rectification column, 6 refers to third rectification column, 7 refers to fourth rectification column, 8 to 22 represents process pipelines.

DETAILED DESCRIPTION OF THE EMBODIMENTS

The process of the invention is shown in FIG. 1. The raw material cis-1-chloro-3,3,3-trifluoropropene (HFO-1233zd (Z)) enters a first reactor 1 through a pipeline 8 for reaction to obtain a mixture containing HFO-1233zd(E) and unreacted HFO-1233zd(Z); the mixture is introduced into a pipeline 9 to enter a first rectification column 2; a product HFO-1233zd(E) is taken from the overhead of the first rectification column 2 through a pipeline 10, and unreacted HFO-1233zd(Z) at the bottom of the first rectification column 2 is returned to the first reactor 1 through a pipeline 11; 30 to 70 wt % of HFO-1233zd(E) enters a second reactor 3 through a pipeline 12, and HF enters the second reactor through a pipeline 13 for reaction to obtain a mixture containing HFO-1234ze(E), HFO-1234ze(Z), HFC-245fa, unreacted HFO-1233zd(E), HCL and HF, and the mixture enters a phase separator 4 through a pipeline 14; an inorganic phase containing a large amount of HF and a small amount of organics at the upper layer of the phase separator 4 is returned to the second reactor 3 through a pipeline 15, and an organic phase containing a large amount of organics and a small amount of HF at the bottom layer of the phase separator 4 enters a second rectification column 5 through a pipeline 16, an overhead component of the second rectification column 5 is the product HFO-1234ze(E) and taken out through a pipeline 17, and a mixture containing HFO-1234ze(Z), HFC-245fa and unreacted HFO-1233zd(E) at the bottom of the second rectification column 5 enters a third rectification column 6 through a pipeline 18; an overhead component of the third rectification column 6 is the product HFO-1234ze(Z) and taken out through a pipeline 19, and a mixture containing HFC-245fa and unreacted HFO-1233zd (E) at the bottom of the third rectification column 6 enters a fourth rectification column 7 through a pipeline 20; an overhead component of the fourth rectification column 7 is product HFC-245fa and taken out through a pipeline 21, and unreacted HFO-1233zd(E) at the bottom of the fourth rectification column 7 is returned to the second reactor 3 through a pipeline 22.

The invention is further described in detail below with reference to embodiments, but the invention is not limited to the following embodiments.

Embodiment 1

200 ml of an $Al_2O_3$/Cr/Mg catalyst (by mass percentage, composition: 95% of $Al_2O_3$; 4% of $Cr_2O_3$; 1% of MgO) is loaded into a first reactor, and the temperature is raised to a bed temperature of 330° C., and HF is introduced for activation at a HF flow rate of 100 g/h and at a hot spot temperature of less than 380° C.; when the hot spot temperature and the bed temperature are the same but no longer raised, the fluorination ends.

The first reactor is heated to the reaction temperature, and HFO-1233zd(Z) is introduced to carry out a reaction, the space velocity of the reactor is maintained at a set value, and after 1 hour of reaction, samples are taken from the outlet of the first reactor for analysis. The reaction results at different temperatures and space velocities are shown in Table 1-1.

TABLE 1-1

| Outlet Organic Composition of the First Reactor in Embodiment 1 | | | | |
|---|---|---|---|---|
| Reaction conditions | | Outlet composition of reactor (%) | | |
| Temperature (° C.) | Space velocity ($h^{-1}$) | HFO-1233zd (Z) | HFO-1233zd (E) | Other |
| 200 | 500 | 63.5 | 36.4 | 0.1 |
| 250 | 300 | 53.4 | 46.5 | 0.1 |
| 320 | 800 | 44.6 | 55.2 | 0.2 |
| 400 | 1000 | 32.7 | 67 | 0.3 |
| 260 | 500 | 49.1 | 50.8 | 0.1 |

200 ml of a $Cr_2O_3$/ZnO/GaO catalyst (by mass percentage, composing 80% of $Cr_2O_3$, 19% of ZnO and 1% of GaO) is loaded into a second reactor, and the temperature is raised to a bed temperature of 350° C., and HF is introduced for activation at a HF flow rate of 100 g/h and at a hot spot temperature of less than 370° C.; when the hot spot temperature and the bed temperature are the same but no longer raised, the fluorination is further carried out for 20 h and then ends.

After separating the outlet mixture of the first reactor, a product HFO-1233zd(E) with the purity of 99.9% is obtained, and 30 wt % of the product HFO-1233zd(E) is introduced into the second reactor together with HF to carry out reaction; and after 1 hour of reaction, samples are taken from the outlet of the second reactor for analysis. The results of the reaction under the conditions of different temperatures, space velocities, and molar ratios of HF to trans-1-chloro-3,3,3-trifluoropropene are shown in Table 1-2.

TABLE 1-2

| Outlet Organic Composition of the Second Reactor in Embodiment 1 | | | | | | | |
|---|---|---|---|---|---|---|---|
| Temperature (° C.) | Space velocity ($h^{-1}$) | HF/HFO-1233zd (E) | HFO-1233zd (E) | HFO-1234ze (E) | HFO-1234ze (Z) | HFC-245fa | Other |
| 180 | 500 | 10 | 54.7 | 1.5 | 0.5 | 43.2 | 0.1 |
| 200 | 300 | 8 | 36.9 | 3.6 | 0.8 | 58.6 | 0.1 |
| 300 | 700 | 15 | 52.2 | 10.9 | 1.2 | 35.6 | 0.1 |
| 350 | 700 | 20 | 45.1 | 28.7 | 1.8 | 24.2 | 0.2 |
| 400 | 500 | 10 | 41.6 | 43.2 | 2.6 | 12.3 | 0.3 |
| 230 | 500 | 10 | 30.1 | 1.1 | 0.2 | 68.5 | 0.1 |
| 330 | 600 | 12 | 36.3 | 50.2 | 2.8 | 10.5 | 0.2 |

Embodiment 2

200 ml of an $Al_2O_3$/Cr/Mg catalyst (by mass percentage, comprising 90% of $Al_2O_3$, 8% of $Cr_2O_3$ and 2% of MgO) is loaded into a first reactor, and the temperature is raised to a bed temperature of 330° C., and HF is introduced for activation at a HF flow rate of 100 g/h and at a hot spot temperature of less than 380° C.; when the hot spot temperature and the bed temperature are the same but no longer raised, the fluorination ends.

The first reactor is heated to the reaction temperature, and HFO-1233zd(Z) is introduced to carry out a reaction, the space velocity of the reactor is maintained at a set value, and after 1 hour of reaction, samples are taken from the outlet of the first reactor for analysis. The reaction results at different temperatures and space velocities are shown in Table 2-1.

TABLE 2-1

Outlet Organic Composition of the First Reactor in Embodiment 2

| Reaction conditions | | Outlet composition of reactor (%) | | |
|---|---|---|---|---|
| Temperature (° C.) | Space velocity (h$^{-1}$) | HFO-1233zd (Z) | HFO-1233zd (E) | Other |
| 200 | 500 | 55.6 | 44.3 | 0.1 |
| 250 | 300 | 48.6 | 51.3 | 0.1 |
| 320 | 800 | 32.2 | 67.5 | 0.3 |
| 400 | 1000 | 14.5 | 85.1 | 0.4 |
| 260 | 500 | 37.5 | 62.4 | 0.1 |

200 ml of a $Cr_2O_3$/ZnO/GaO catalyst (by mass percentage, comprising 90% of $Cr_2O_3$, 9.5% of ZnO and 0.5% of GaO) is loaded into a second reactor, and the temperature is raised to a bed temperature of 350° C., and HF is introduced for activation at a HF flow rate of 100 g/h and at a hot spot temperature of less than 370° C.; when the hot spot temperature and the bed temperature are the same but no longer raised, the fluorination is further carried out for 20 h and then ends.

After separating the outlet mixture of the first reactor, a product HFO-1233zd(E) with the purity of 99.9% is obtained, and 40 wt % of the product HFO-1233zd(E) is introduced into the second reactor together with HF to carry out reaction; and after 1 hour of reaction, samples are taken from the outlet of the second reactor for analysis. The results of the reaction under the conditions of different temperatures, space velocities, and molar ratios of HF to trans-1-chloro-3,3,3-trifluoropropene are shown in Table 2-2.

TABLE 2-2

Outlet Organic Composition of the Second Reactor in Embodiment 2

| Temperature (° C.) | Space velocity (h$^{-1}$) | HF/HFO-1233zd (E) | HFO-1233zd (E) | HFO-1234ze (E) | HFO-1234ze (Z) | HFC-245fa | Other |
|---|---|---|---|---|---|---|---|
| 180 | 500 | 10 | 50 | 1.1 | 0.3 | 48.5 | 0.1 |
| 200 | 300 | 8 | 30.8 | 2.7 | 05 | 61.4 | 0.1 |
| 300 | 700 | 15 | 51.8 | 15.6 | 1.7 | 30.8 | 0.1 |
| 350 | 700 | 20 | 40.8 | 37.5 | 2.5 | 19 | 0.2 |
| 400 | 500 | 10 | 35.2 | 51.7 | 3.2 | 9.5 | 0.4 |
| 230 | 500 | 10 | 21.3 | 0.9 | 0.1 | 77.6 | 0.1 |
| 330 | 600 | 12 | 25.2 | 62.1 | 5.8 | 6.7 | 0.2 |

Embodiment 3

200 ml of an $Al_2O_3$/Cr/Mg catalyst (by mass percentage, comprising 93% of $Al_2O_3$, 6% of $Cr_2O_3$ and 1% of MgO) is loaded into a first reactor, and the temperature is raised to a bed temperature of 330° C., and HF is introduced for activation at a HF flow rate of 100 g/h and at a hot spot temperature of less than 380° C.; when the hot spot temperature and the bed temperature are the same but no longer raised, the fluorination ends.

The first reactor is heated to the reaction temperature, and HFO-1233zd(Z) is introduced to carry out a reaction, the space velocity of the reactor is maintained at a set value, and after 1 hour of reaction, samples are taken from the outlet of the first reactor for analysis. The reaction results at different temperatures and space velocities are shown in Table 3-1.

TABLE 3-1

Outlet Organic Composition of the First Reactor in Embodiment 3

| Reaction conditions | | Outlet composition of reactor (%) | | |
|---|---|---|---|---|
| Temperature (° C.) | Space velocity (h$^{-1}$) | HFO-1233zd (Z) | HFO-1233zd (E) | Other |
| 200 | 500 | 67.1 | 32.8 | 0.1 |
| 250 | 300 | 58.4 | 41.5 | 0.1 |
| 320 | 800 | 50.9 | 48.9 | 0.2 |
| 400 | 1000 | 40.1 | 59.7 | 0.2 |
| 260 | 500 | 55.6 | 44.3 | 0.1 |

200 ml of a $Cr_2O_3$/ZnO/GaO catalyst (by mass percentage, comprising 73% of $Cr_2O_3$, 25% of ZnO and 2% of GaO) is loaded into a second reactor, and the temperature is raised to a bed temperature of 350° C., and HF is introduced for activation at a HF flow rate of 100 g/h and at a hot spot temperature of less than 370° C.; when the hot spot temperature and the bed temperature are the same but no longer raised, the fluorination is further carried out for 20 h and then ends.

After separating the outlet mixture of the first reactor, a product HFO-1233zd(E) with the purity of 99.9% is obtained, and 50 wt % of the product HFO-1233zd(E) is introduced into the second reactor together with HF to carry out reaction; and after 1 hour of reaction, samples are taken from the outlet of the second reactor for analysis. The results of the reaction under the conditions of different temperatures, space velocities, and molar ratios of HF to trans-1-chloro-3,3,3-trifluoropropene are shown in Table 3-2.

TABLE 3-2

Outlet Organic Composition of the Second Reactor in Embodiment 3

| Temperature (° C.) | Space velocity (h$^{-1}$) | HF/HFO-1233zd (E) | HFO-1233zd (E) | HFO-1234ze (E) | HFO-1234ze (Z) | HFC-245fa | Other |
|---|---|---|---|---|---|---|---|
| 180 | 500 | 10 | 47.0 | 1.2 | 0.4 | 51.3 | 0.1 |
| 200 | 300 | 8 | 29.3 | 3.1 | 0.3 | 67.2 | 0.1 |
| 300 | 700 | 15 | 50.5 | 21.3 | 2.2 | 25.9 | 0.1 |

TABLE 3-2-continued

Outlet Organic Composition of the Second Reactor in Embodiment 3

| Temperature (° C.) | Space velocity ($h^{-1}$) | HF/HFO-1233zd (E) | HFO-1233zd (E) | HFO-1234ze (E) | HFO-1234ze (Z) | HFC-245fa | Other |
|---|---|---|---|---|---|---|---|
| 350 | 700 | 20 | 48.0 | 44.1 | 2.1 | 5.6 | 0.2 |
| 400 | 500 | 10 | 25.1 | 65.8 | 2.3 | 6.5 | 0.3 |
| 230 | 500 | 10 | 24.2 | 1.2 | 0.3 | 74.2 | 0.1 |
| 330 | 600 | 12 | 31.7 | 60.4 | 1.5 | 6.2 | 0.2 |

Embodiment 4

200 ml of an $Al_2O_3$/Cr/Mg catalyst (by mass percentage, comprising 90% of $Al_2O_3$, 7% of Cr and 3% of Mg) is loaded into a first reactor, and the temperature is raised to a bed temperature of 330° C., and HF is introduced for activation at a HF flow rate of 100 g/h and at a hot spot temperature of less than 380° C.; when the hot spot temperature and the bed temperature are the same but no longer raised, the fluorination ends.

The first reactor is heated to the reaction temperature, and HFO-1233zd(Z) is introduced to carry out a reaction, the space velocity of the reactor is maintained at a set value, and after 1 hour of reaction, samples are taken from the outlet of the first reactor for analysis. The reaction results at different temperatures and space velocities are shown in Table 4-1.

TABLE 4-1

Outlet Organic Composition of the First Reactor in Embodiment 4

| Reaction conditions | | Outlet composition of reactor (%) | | |
|---|---|---|---|---|
| Temperature (° C.) | Space velocity ($h^{-1}$) | HFO-1233zd (Z) | HFO-1233zd (E) | Other |
| 200 | 500 | 52.5 | 47.5 | 0 |
| 250 | 300 | 46.1 | 53.8 | 0.1 |
| 320 | 800 | 24.5 | 75.3 | 0.2 |
| 400 | 1000 | 14.2 | 85.7 | 0.1 |
| 220 | 500 | 18.6 | 81.3 | 0.1 |

200 ml of a $Cr_2O_3$/ZnO/GaO catalyst (by mass percentage, comprising 85% of $Cr_2O_3$, 14% of ZnO and 1% of GaO) is loaded into a second reactor, and the temperature is raised to a bed temperature of 350° C., and HF is introduced for activation at a HF flow rate of 100 g/h and at a hot spot temperature of less than 370° C.; when the hot spot temperature and the bed temperature are the same but no longer raised, the fluorination is further carried out for 20 h and then ends.

After separating the outlet mixture of the first reactor, a product HFO-1233zd(E) with the purity of 99.9% is obtained, and 70 wt % of the product HFO-1233zd(E) is introduced into the second reactor together with HF to carry out reaction; and after 1 hour of reaction, samples are taken from the outlet of the second reactor for analysis. The results of the reaction under the conditions of different temperatures, space velocities, and molar ratios of HF to trans-1-chloro-3,3,3-trifluoropropene are shown in Table 4-2.

TABLE 4-2

Outlet Organic Composition of the Second Reactor in Embodiment 4

| Temperature (° C.) | Space velocity ($h^{-1}$) | HF/HFO-1233zd (E) | HFO-1233zd (E) | HFO-1234ze (E) | HFO-1234ze (Z) | HFC-245fa | Other |
|---|---|---|---|---|---|---|---|
| 180 | 500 | 10 | 43.7 | 0.8 | 0.2 | 55.2 | 0.1 |
| 200 | 300 | 8 | 23.2 | 1.1 | 0.5 | 75.1 | 0.1 |
| 300 | 700 | 15 | 17.5 | 35.3 | 1.8 | 45.3 | 0.1 |
| 350 | 700 | 20 | 34.2 | 51.6 | 1.6 | 12.3 | 0.3 |
| 400 | 500 | 10 | 13.8 | 74.6 | 1.9 | 9.6 | 0.1 |
| 230 | 500 | 10 | 13.2 | 0.9 | 0.7 | 85.2 | 0 |
| 350 | 600 | 10 | 4.5 | 81.2 | 5.6 | 8.5 | 0.2 |

What is claimed is:

1. A method for co-producing alkenyl halides and hydrofluoroalkanes, comprising following steps of:
    (a) introducing cis-1-chloro-3,3,3-trifluoropropene into a first reactor where an isomerization reaction occurs in the presence of a first catalyst to obtain a first reactor reaction product, wherein a temperature of the isomerization reaction is 200-400° C., and an air velocity of the isomerization reaction is 300-1000 $h^{-1}$;
    (b) introducing the first reactor reaction product obtained in the Step (a) into a first rectification column to obtain a product of trans-1-chloro-3,3,3-trifluoropropene and a first rectification column bottom liquid;
    (c) mixing 30-70 wt % of the trans-1-chloro-3,3,3-trifluoropropene obtained in the Step (b) with hydrogen fluoride, and then introducing the trans-1-chloro-3,3,3-trifluoropropene and the hydrogen fluoride in a second reactor where a reaction occurs in the presence of a catalyst to obtain a second reactor reaction product, wherein a molar ratio of the hydrogen fluoride to the trans-1-chloro-3,3,3-trifluoropropene is 8-20:1, a temperature of the reaction is 180-400° C., and a space velocity of the reaction is 300-1000 $h^{-1}$;
    (d) introducing the second reactor reaction product obtained in the Step (c) into a phase separator for separation to obtain an inorganic phase and an organic phase;
    (e) introducing the organic phase obtained in the Step (d) into a second rectification column to obtain a product of trans-1,3,3,3-tetrafluoropropene and a second rectification column bottom liquid;

(f) introducing the second rectification column bottom liquid obtained in the Step (e) into a third rectification column to obtain a product of cis-1,3,3,3-tetrafluoropropene and a third rectification column bottom liquid; and (g) introducing the third rectification column bottom liquid obtained in the Step (f) into a fourth rectification column to obtain a product of 1,1,1,3,3-pentafluoropropane and a fourth rectification column bottom liquid.

2. The method for co-producing alkenyl halides and hydrofluoroalkanes according to claim 1, wherein the first rectification column bottom liquid in the Step (b) is recycled back to the first reactor.

3. The method for co-producing alkenyl halides and hydrofluoroalkanes according to claim 1, wherein the inorganic phase in the Step (d) is recycled back to the second reactor.

4. The method for co-producing alkenyl halides and hydrofluoroalkanes according to claim 1, wherein the fourth rectification column bottom liquid in the Step (g) is recycled back to the second reactor.

5. The method for co-producing alkenyl halides and hydrofluoroalkanes according to claim 1, wherein in the Step (a) the temperature of the isomerization reaction is 250-320° C., and the air velocity of the isomerization reaction is 500-800 $h^{-1}$.

6. The method for co-producing alkenyl halides and hydrofluoroalkanes according to claim 1, wherein in the Step (c) the molar ratio of the hydrogen fluoride to the trans-1-chloro-3,3,3-trifluoropropene is 10-15:1, the temperature of the reaction is 200-350° C., and the space velocity of the reaction is 500-700 $h^{-1}$.

7. The method for co-producing alkenyl halides and hydrofluoroalkanes according to claim 1, wherein the first catalyst in the Step (a) is alumina-loaded chromium and magnesium, wherein the load of chromium is 3-8 wt %, and the load of magnesium is 1-3 wt %.

8. The method for co-producing alkenyl halides and hydrofluoroalkanes according to claim 1, wherein a composition of the second catalyst in the Step (c) comprises, by mass percentage, 73-90% of chrome oxide, 9.5-25% of zinc oxide, and 0.5-2% of gallium oxide.

* * * * *